United States Patent [19]

Kalt

[11] Patent Number: 4,919,654
[45] Date of Patent: Apr. 24, 1990

[54] IV CLAMP WITH MEMBRANE

[75] Inventor: Glenda G. Kalt, Boca Raton, Fla.

[73] Assignee: Kalt Medical Corporation, Boca Raton, Fla.

[21] Appl. No.: 227,784

[22] Filed: Aug. 3, 1988

[51] Int. Cl.$^5$ .......................................... A61M 25/02
[52] U.S. Cl. ............................. 604/180; 128/DIG. 26
[58] Field of Search ....................... 604/180, 174, 179; 128/DIG. 15, DIG. 16, DIG. 26; 24/306, 442

[56] References Cited

U.S. PATENT DOCUMENTS

| | | |
|---|---|---|
| 2,273,873 | 2/1942 | Klein . |
| 2,707,953 | 5/1955 | Ryan . |
| 2,735,432 | 2/1956 | Hudson . |
| 2,949,443 | 8/1960 | Merriam et al. . |
| 3,046,989 | 7/1962 | Hill . |
| 3,059,645 | 10/1962 | Hasbrouck et al. . |
| 3,161,199 | 12/1964 | Shaw . |
| 3,288,136 | 11/1966 | Lund . |
| 3,324,853 | 6/1967 | Czorny et al. . |
| 3,630,195 | 12/1971 | Santomieri . |
| 3,677,250 | 7/1972 | Thomas . |
| 3,696,920 | 10/1972 | Lahay . |
| 3,702,612 | 11/1972 | Schlesinger . |
| 3,782,383 | 1/1972 | Thompson et al. . |
| 3,826,254 | 7/1974 | Mellor . |
| 3,834,380 | 9/1974 | Boyd . |
| 3,918,446 | 11/1975 | Buttaravoli . |
| 3,972,321 | 8/1976 | Proctor . |
| 4,018,221 | 4/1977 | Rennie . |
| 4,074,397 | 2/1978 | Rosin . |
| 4,088,136 | 5/1978 | Hasslinger . |
| 4,122,857 | 10/1978 | Haerr . |
| 4,142,527 | 3/1979 | Garcia . |
| 4,165,748 | 8/1979 | Johnson . |
| 4,181,127 | 1/1980 | Linsky et al. . |
| 4,324,237 | 4/1982 | Buttaravoli ........................ 604/180 |
| 4,329,984 | 5/1982 | Kervin . |
| 4,333,468 | 6/1982 | Geist . |
| 4,341,208 | 7/1982 | Gordon . |
| 4,416,664 | 11/1983 | Womack . |
| 4,417,710 | 11/1983 | Adair . |
| 4,485,809 | 12/1984 | Dellas . |
| 4,534,762 | 8/1985 | Heyer . |
| 4,583,976 | 4/1986 | Ferguson . |
| 4,617,017 | 10/1986 | Hubbard et al. . |
| 4,669,458 | 6/1987 | Abraham et al. ................... 604/180 |
| 4,744,355 | 5/1988 | Faasse, Jr. . |

FOREIGN PATENT DOCUMENTS 998901 10/1976 Canada .

OTHER PUBLICATIONS

Dale Endotracheal Tube Holders for Oral Intubation Instruction Sheet No. 507, ©1985, Rev. 4/87.
"Product News," description of Cath-Secure by M. C. Johnson Co., Inc.
The 3-M TEGADERM Transparent Dressing Brochure by the 3-M Company.
Conmed VENIGARD Disposable Dressing Disclosure.

*Primary Examiner*—Stephen C. Pellegrino
*Attorney, Agent, or Firm*—Dickstein, Shapiro & Morin

[57] ABSTRACT

A clamp for holding an article to an object including a base means for adhering the clamp to the object, a flap, securing means for securing the flap to the base with the article positioned therebetween and resilient pad having an adhesive surface for contacting the article. Resilient adhesive surfaces are provided on the flap and base for contacting and adhering the article.

19 Claims, 3 Drawing Sheets

IV CLAMP WITH MEMBRANE

BACKGROUND OF THE INVENTION

The present invention relates in general to a clamp for holding an article and more particularly to a medical clamp for holding a tube or IV needle to a patient's body.

It is often necessary to clamp external and mesentery tubes and lines to a medical patient's body, for example, feeding tubes, naso-gastric tubes, chest tubes, foley catheter as well as condom catheter tubes, dialysis tubes, endotracheal tubes, pressure monitoring devices, angiocath and heparin lock set tubes, as well as other tubes and lines used to introduce fluids into the body intravenously or to introduce oxygen into the mouth or nose of a patient.

It is important that a tube clamp holds the tube or line firmly because movement of the tubes or lines may cause discomfort to the patient. It is often necessary to remove the tube and replace it with another or to adjust the position of the tube or line. Therefore, it is desirable that the clamp be releasable so that the tube or line may be unclamped and reclamped without removing or replacing the entire clamp structure.

U.S. Pat. No. 3,826,254 discloses a clamp comprising an adhesive pad which folds back over itself to adhere a tube.

U.S. Pat. No. 4,165,748 discloses a tube clamp formed in one piece and adhered to a patient's body and having a center portion which folds around and clamps the tube by adhering to itself.

U.S. Pat. No. 4,333,468 discloses a clamp having a base having two raised portions to form between them a transverse groove. A tube is accepted to lie in the groove and a flap permanently affixed to the base at one end is extendable over the tube. Pressure sensitive adhesive covers the raised portions and the groove of the base as well as the flap underside. The flap is pressed onto the raised portions and the tube to adhere and clamp the tube in the groove.

Each of the foregoing clamps suffers the disadvantage that slight rotation or translation of the tube tends to break the adhesive bond. Thus secure holding of the tube is not effected.

U.S. Pat. No. 3,834,380 discloses a clamp including a slit tube which receives a rod-like article and is closed and kept closed by a flap attached to the tube at one end and secured at the other end. The tube is flexible and may be resilient. This device is unduly bulky and may cause discomfort to the patient and tends to lift the clamp tape off of the patient which causes further discomfort. However, this device is insufficiently flexible for use in areas of the body where movement is likely and flexibility is desired. Such areas include the head and joint areas. This inflexibility may result in a tube being held in a wrong position. Moreover, this device depends on friction for holding a tube, and is therefore dependent upon the surface properties of the article or tube to be held to effect such a friction bond. If the surface of the article to be held is "slippery" relative to the material of the slit tube, the holding effect will be poor. A further disadvantage of this device is that only a small range of sizes of tubes may be held for a given slit tube size.

Haerr, U.S. Pat. No. 4,122,857 discloses a substantially rectangular pad of soft, strong, flexible, foam material provided with a secure flap by which an article such as a catheter tube or the like may be anchored to the pad which in turn is adapted to be adhesively affixed to the skin of the patient.

SUMMARY OF THE INVENTION

The present invention alleviates to a great extent the disadvantages of prior devices by providing a clamp for holding an article to an object including a base means for adhering the clamp to the object, a flap, securing means for securing a flap to the base means with the article positioned therebetween, and resilient pad means having an adhesive surface for contacting the article. In one aspect of the invention, the securing means includes a first holding means for holding a first portion of the flap and a second holding means for holding a second portion of the flap. The second holding means is spaced along the flap from the first holding means a sufficient distance for the article to lie between them. The resilient pad means is deformable such that slight rotational or translational movement will deform the pad rather than break the adhesive bond between the pad and the article.

In another aspect of the invention, the base means has a base window formed therein for positioning the clamp on the patient with the IV puncture positioned to be viewed through the window.

It is an object of the present invention to provide a clamp for holding an article.

It is a further object of the present invention to provide a clamp having a resilient adhesive pad in contact with the held article to inhibit the breaking of the adhesive bond as a result of rotational or translational movement of the article.

It is another object of the invention to provide a medical clamp to releasably hold a tube or line and to allow removal of the tube or line and repositioning of the tube or line without removal of the clamp from the patient's body.

It is yet another object of the invention to provide a medical clamp yielding the foregoing advantages and that effectively holds a tube against transverse and rotational movement.

It is still another object of the present invention to provide a medical clamp yielding the foregoing advantages and that is simply and economically constructed.

It is still further object of the present invention to provide a medical clamp yielding the foregoing advantages and that can clamp a variety of sizes of tubes.

DETAILED DESCRIPTION OF THE PREFERRED EMBODIMENTS

As referred to herein, the inner surfaces of various component parts of the preferred embodiments of the present invention are those surfaces oriented towards the object to which the clamp is adhered. Similarly, the outer surfaces of the various component parts of the preferred embodiment are those surfaces oriented away from such object. Such object may be any object but for medical clamps will most likely be the patient's skin, the patient's clothing, bandages, casts or the like.

Figure 3:
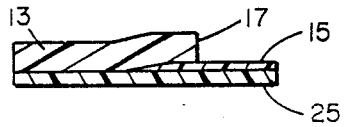
FIG. 3 is a view taken along Section line III—III of FIG. 1.

Referring now to FIGS. 1 through 5, therein is shown a medical clamp, generally designated by reference numeral 10, according to a preferred embodiment of the present invention. In the preferred embodiment, the clamp 10 is particularly suitable for holding an IV tube 22 to the skin of a medical patient. The base means for adhering clamp 10 to the patient includes a base 12 that is preferably composed of an adhesive, stretchable, polymer material such as is marketed by Conmed Corporation under the registered trademark "MACROLYTE", or an adhesive, stretchable, hypoallergenic foam material marketed by 3M Company under the registered trademark "MICROFOAM" or medical grade tape such as 3M-1527L marketed by 3M Company under the registered trademark "Transpore". Base 12 is coated on its inner surface 24, with a medical grade adhesive, preferable a hypoallergenic synthetic acrylic pressure sensitive adhesive. A protective liner 25 is provided to extend over and protect the inner surface 24 and membrane 15 until the clamp is used. The base 12 includes an arch portion 13 forming a window opening 17. A sterile, breathable, clear, waterproof, membrane 15 extends over the window opening 17 and overlaps and is adhered to the base arch 13 on its inner surface 24 as shown in FIG. 3. A membrane marketed by 3M Company under the trademark "TEGADERM" is suitable to use for the membrane 15. The use of a membrane 15 with the arch 13 seals and protects the skin puncture 90 by the needle 9, which extends through the membrane 15 at puncture hole 18. The arch 13 of clamp 10 is wider near flap 20 to give arch 13 structure that is less inclined to be pulled away from the skin.

Figure 1:
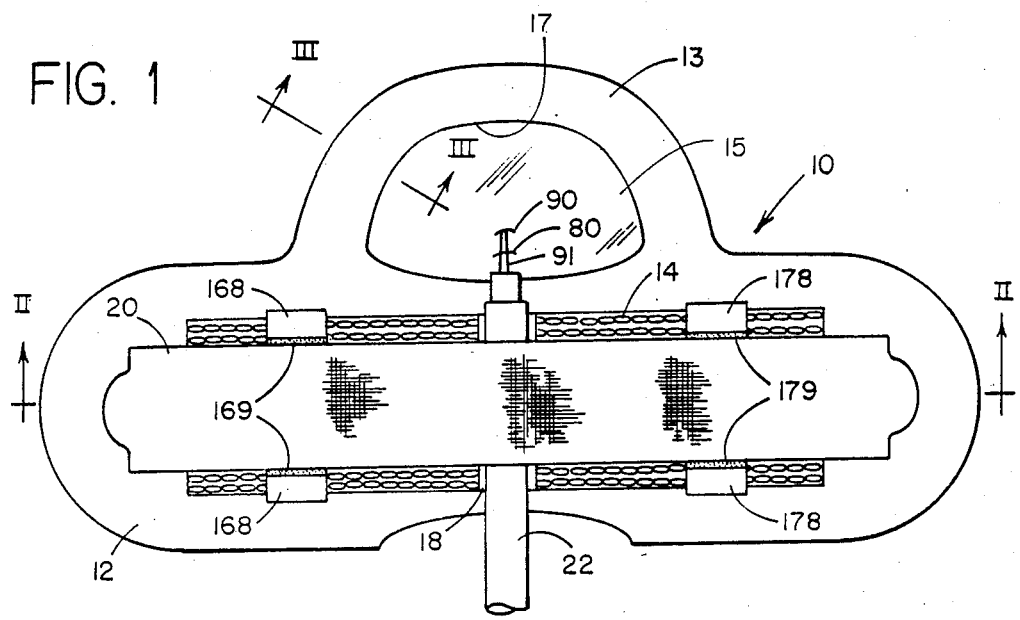
FIG. 1 is a plan view of a preferred embodiment of a clamp according to the present invention.
Figure 2:
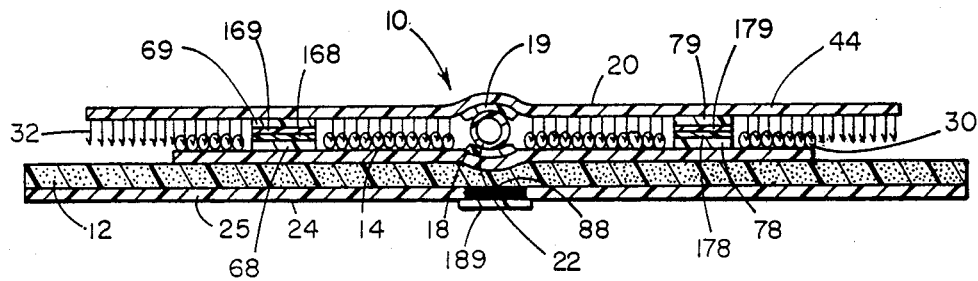
FIG. 2 is a view taken along section line II—II of FIG. 1.

As shown in FIG. 1, the flap 20 extends outside the tube 22 and is secured to the base 12 by securing means to hold the tube 22 therebetween. In the first preferred embodiment, securing means includes hook and loop fastening material 32 and 30 as described in more detail below. The flap 20 includes a hook base fabric 34 into which is woven hooks 32 of the securing means.

The loop pad 14 is composed of a loop material that includes a loop fabric 30 which is woven into a base fabric 28. The pad 14 is adhered to the base 12 by medical grade adhesive. The loop pad 14 is adapted to mate with the hook pad 44 to secure the flap 20 to the base 12. The tube 22 extends along the resilient adhesive pads 18 and 19 between the flap 20 and the base 12.

The hook and loop materials are available from 3M Company under the registered trademark "Scotchmate". Resilient adhesive pads 18, 68 and 78 are formed by applying a hot melt adhesive to the loop fabric 30 such that the applied adhesive extends up slightly above the top of the loops. Resilient pads 19, 69 and 79 are formed by applying a hot melt adhesive to the hook fabric 32 such that the applied adhesive extends up slightly above the top of the hooks. When the hot melt adhesive cools and cures, it forms a resilient pad with an adhering outer surface. A resilient adhesive pad 88 is provided on the inside surface 24 of base 12 for use as described below with respect to FIG. 4. Liners 118, 119, 168, 169, 170 and 179 and 189 are provided to protect the resilient pads prior to use. Medical grade hot melt adhesives suitable for this purpose include numbers DD5800, DD5900, DD5914 available from H. Fuller Adhesive Company. Preferably, the applied hot melt adhesive, when set up, or cured, will extend about one sixteenth of an inch above the loop or hook material surface.

In the preferred embodiment the loop material has been provided to face outwards because loop material is typically softer than hook material and will not discomfort the patient if her skin should rub against it.

With reference to commonly owned U.S. patent application Ser. No. 086,473, filed Aug. 18, 1987, the disclosure of which is incorporated by reference, it has been found that the utilization of a resilient adhesive pad in contact with a tube or IV needle structure provides a secure means for holding the tube or structure against rotational or translational movement. This may be because in use the resilient material tends to deform and twist through its thickness and move with the tube when the tube is urged to rotate slightly or to translate slightly. Because the resilient material deforms, the bond of the adhesive with the tube is stressed to a lesser degree and is less likely to be broken. Significant deformation must occur before the resilient material will resist further deformation with such a force that the adhesive bond between the pad and the tube is broken. Accordingly, significant movement of the tube is possible prior to the breaking of the adhesive bond. Conversely, in prior clamps where no resilient adhesive pads are provided, any rotational or translational movement of the tube, with respect to the clamp adhesive surfaces, which movement may be caused by the bumping of the tube by the patient, may more likely result in the breaking of the adhesive bond holding the tube. The adhesive surface of clamps formed of a continuous foam material covered with an adhesive layer tends to pull away from and separate from the tube or IV clamp due to the stretching of the adhesive surface.

Figure 4:
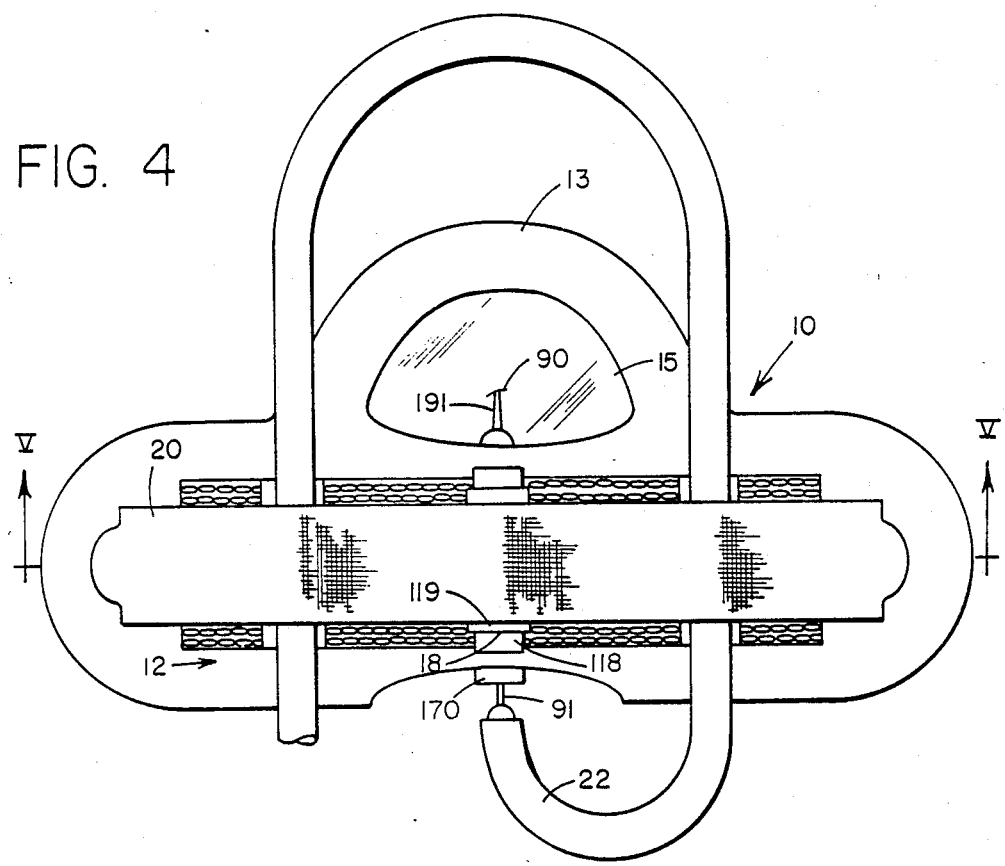
FIG. 4 is a view like FIG. 1 illustrating an alternate arrangement for clamping a needle and tube.
Figure 5:
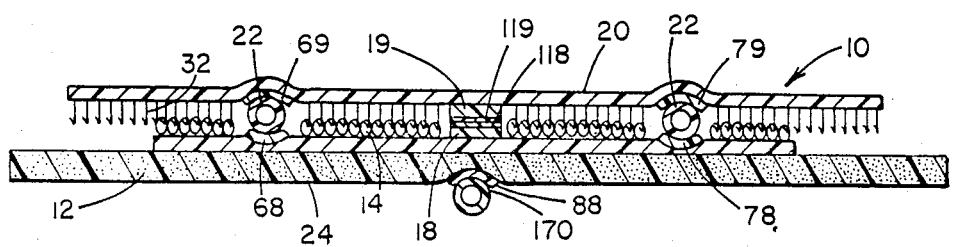
FIG. 5 is a view taken along section line V—V of FIG. 4.

Refer now to FIGS. 4 and 5 therebeing shown clamp 10 used in a different manner. In FIGS. 4 and 5, clamp 10 is folding IV 170 between the base and the skin of the patient. The needle 191 of the IV 170 extends under the clear membrane 15 to puncture the flesh at puncture 90. The IV needle 91 is inserted into a self sealing type IV needle 170. Tube 22 is held by pads 68, 78, 69 and 79 of the base 12 and the clamp 20, respectively. IV 170 is held by resilient adhesive pad 88 from which protective liner 188 (FIG. 2) has been removed. The tube 22 is looped around to lie over and between the resilient adhesive pads to provide further resilient holding of the tube to decrease the likelihood of the IV 170 being moved upon inadvertent jostling of the tube 22. As a result of the additional holding of tube 22 by the pads 68, 78, 69 and 79, the adhesive pad 88 may alternately be dispensed with so that the adhesive surface 24 of the base 12 extends over and contacts the IV 170. Liners 118 and 119 are shown in place protecting resilient adhesive pads 18 and 19 when not in use.

Figure 6:
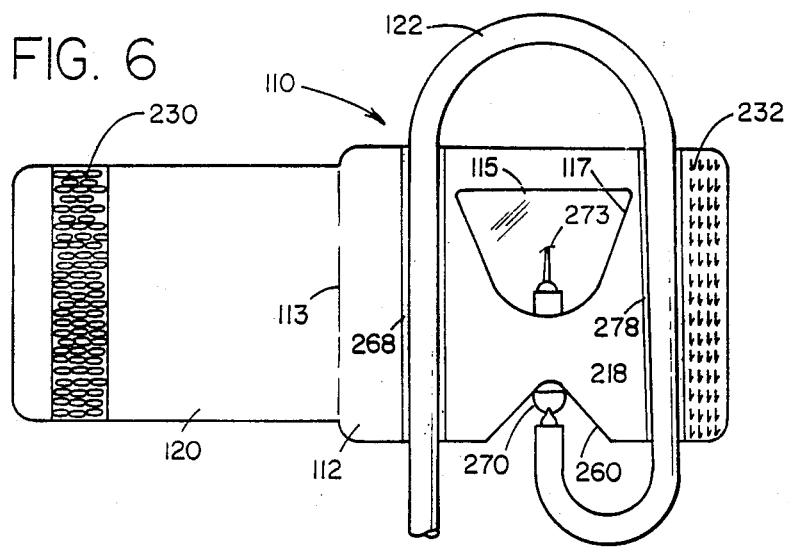
FIG. 6 is a plan view of an alternate embodiment of a clamp according to the present invention.

Refer now to FIG. 6 there being shown an alternate embodiment of the present invention, generally designated by reference numeral 110, particularly adapted for use with so called hepburn type locks for catheter needles. These locks are used when an intravenous needle is left in place over an extended time or in lines that are under increased pressure such a arterial lines and provides a coupling for removably attaching various other needles and/or tubes for supplying medication, nourishment and the like. These locks may require access to locking mechanisms for operating the devices between open and closed positions and/or, these locks may be self sealing when the needle is removed.

Clamp 110 includes a base 112 having an adhesive lower surface protected with a liner which is removable for attaching the clamp 110 to the patient via base 112. The base substrate material has hook material 232 woven into it. A flap 120 is composed of material such as "MEDIPORE" marketed by 3-M Company, "MACROLYTE" marketed by Conmed Company or "MICROFOAM" marketed by 3-M Company. Flap 120 is adhered to the edge 113 of base 112 and widens from edge 113 to a protruding portion 125 and then narrows to a tab portion 129. A loop material 230 is woven to the tab portion 129 although area 129 may be left free of loop material for slightly easier gripping.

A clear membrane 115 similar in construction to the membrane 15 discussed above, extends under window opening 117 formed in the base 112 and over the puncture 273 caused by the IV needle 270. The protruding portion 125 of the flap 120 lays over the window 115 when the flap 120 is secured with the loop material 230 engaging the hook material 232. The protruding portion is not held down and may be lifted for viewing the puncture 273 without lifting the rest of the flap 120. Resilient adhesive pads 268 and 278, made of a hot melt adhesive, lie adjacent window opening 117. Tube 122 is positioned on pads 268 and 278 as shown in FIG. 6 to provide increased support and isolation for the tube 122 to protect the IV 270 from movement. Slots 260 and 130 allow access to the actuator of a hepburn lock IV 270 if present. Resilient adhesive pad 218, also composed of hot melt adhesive, is also present for holding the IV 270. Note that the loop material 230 engages the hook material 232 for holding the clamp shut. The resilient pad 218 functions to allow some movement of the IV 270 relative to the clamp through the twisting motion of the pad through its thickness. This results in increased comfort to the patient.

In the preferred embodiments of the invention, medical grade adhesive and a hook and loop material is provided to secure the flap to the base, however the present invention is not limited thereto, and other securing means may be used. For example hook material may be used in conjunction with a foam and fabric material. This is sometimes preferable if a somewhat lower holding force is required between the flap and the base. Moreover the fabric and foam material may be more breathable and stretchable than a plastic base material and allow greater air transfer through the clamp to the patient's skin when used thereon.

Also, the clamp as described in the preferred embodiments are shown in a hospital setting, although as already pointed out, the clamps may be used in other settings, medical, medical related and non-medical, for holding articles to objects.

What is new and desired to be protected by Letters Patent of the U.S. is:

1. A clamp for holding an IV device, comprising:
    base means having an arch portion defining a window opening;
    membrane means covering said window opening and having a slot therein for allowing a needle of said IV device to puncture a patient's skin at a point located under said membrane means;
    flap means for covering a tube of said IV device; and
    securing means for securing said flap means to said base means.

2. The clamp of claim 1, wherein said base means has an adhesive inner surface for adhering said clamp to such skin of a medical patient.

3. The clamp of claim 2, wherein said membrane means has an outside surface which partially overlaps and mates with said adhesive inner surface of said base means.

4. The clamp of claim 1, wherein said base means is formed from a stretchable polymer.

5. The clamp of claim 1, wherein said base means is formed from an adhesive, stretchable hypoallergenic foam.

6. The clamp of claim 1, wherein said base means further comprises an arch portion which forms a border around said window opening.

7. The clamp of claim 6, wherein said arch portion is wider toward said flap means in order that said base means is less inclined to pull away from such skin.

8. The clamp of claim 1, wherein said membrane means is made from a sterile, breathable clear waterproof material.

9. The clamp of claim 1, further comprising a protective liner which extends over inner surfaces of said base means and membrane means in order to protect said clamp when not in use.

10. The clamp of claim 1, wherein said securing means comprises a hook material and a loop fastening material.

11. The clamp of claim 10, further comprising an adhesive pad means which is applied to said hook and loop fastening materials such that said adhesive pad means extends up slightly above the top of said securing means.

12. The clamp of claim 11, wherein said adhesive pad means extends one sixteenth inch above said hook and loop materials.

13. The clamp of claim 12, wherein said adhesive pad means is substantially resilient such that rotational and translational movement of said IV tube is hampered and said resilient material tends to deform and twist through its thickness such that significant deformation of said clamp must occur before a bond between said tube and said adhesive pad is broken.

14. The clamp of claim 13, wherein said adhesive pad means are protected by liners in order to cover said adhesive pads when not in use.

15. The clamp of claim 1, further comprising self-sealing needle means located between said flap means and said base means wherein said IV needle is inserted into one end of said self-sealing needle means and an opposite end of said self-sealing needle means is inserted through said membrane into such skin of a medical patient.

16. The clamp of claim 1, wherein said base means and said flap means each have three mutually aligned resilient adhesive pads to provide resilient holding of a self-sealing needle means and a portion of said IV tube such that said IV tube is looped around said clamp and reduces movement of said IV device when stress is applied to said IV tube.

17. The clamp of claim 1, wherein said flap means is adapted to cover an entire outside surface of said base means.

18. A clamp for holding an IV device comprising:
    base means having an adhesive inner surface and defining a window opening;

membrane means extending over said window opening in order to form a sterile, breathable, clear waterproof covering for said window opening;

flap means releasably secured to said base means;

securing means for releasably holding said flap means to said base means; and resilient pad means attached to said base means and flap means wherein said flap means covers a tube of said IV device and holds said tube and a needle of said IV device against rotation or translational movement as said resilient adhesive pad means tends to deform and twist through its thickness.

19. A clamp for holding an article to an object, comprising:

base means having a window opening for adhering the clamp to the object;

a membrane covering said window opening;

a flap;

securing means for securing said flap to said base means with the article positioned therebetween; and resilient pad means adhered to said flap and having an adhesive surface for contacting the positioned article such that a needle attached to a tube forming said article is inserted through said membrane and into said object.

* * * * *